United States Patent [19]

Giertych

[11] Patent Number: 5,605,934
[45] Date of Patent: Feb. 25, 1997

[54] METHOD OF MANUFACTURING AND STORING SOLUTIONS

[75] Inventor: Joseph A. Giertych, Lake Forest, Ill.

[73] Assignee: Baxter International Inc., Deerfield, Ill.

[21] Appl. No.: 409,110

[22] Filed: Mar. 23, 1995

[51] Int. Cl.⁶ .......................... B65B 31/00; A61K 33/10
[52] U.S. Cl. ..................... 424/686; 53/431; 53/434; 514/970
[58] Field of Search ..................... 514/340, 970; 424/686; 53/431, 434; 206/570, 524.1; 210/646, 647

[56] References Cited

U.S. PATENT DOCUMENTS

| | | | |
|---|---|---|---|
| 4,339,433 | 7/1982 | Kartinos et al. | 424/78.18 |
| 4,396,383 | 8/1983 | Hart . | |
| 4,465,488 | 8/1984 | Richmond et al. . | |
| 4,489,535 | 12/1984 | Veltman | 53/431 |
| 4,584,176 | 4/1986 | Oliver et al. . | |
| 4,879,280 | 11/1989 | Seyffart et al. | 514/53 |
| 4,959,175 | 9/1990 | Yatzidis . | |
| 5,039,609 | 8/1991 | Klein | 435/68.1 |
| 5,092,838 | 3/1992 | Faict et al. | 604/27 |
| 5,211,643 | 5/1993 | Reinhardt et al. | 604/416 |
| 5,383,324 | 1/1995 | Segers et al. | 53/425 |

FOREIGN PATENT DOCUMENTS

| | | |
|---|---|---|
| 0209607 | 1/1987 | European Pat. Off. . |
| 0278100 | 6/1988 | European Pat. Off. . |
| 0399549 | 11/1990 | European Pat. Off. . |
| 0399918 | 11/1990 | European Pat. Off. . |
| 0417478 | 3/1991 | European Pat. Off. . |
| 0437274 | 7/1991 | European Pat. Off. . |
| 0481257 | 4/1992 | European Pat. Off. . |

OTHER PUBLICATIONS

Ing et al., "Bicarbonate–Buffered peritoneal Dialysis," in *The International Journal of Artificial Organs*, vol. 8, No. 3, 1985, pp. 121–124.

Murphy et al., "Use of an Artificial Kidney," in *Lab. of Clinical Medicine*, vol. 40, 1952, pp. 436–444.

Yu et al., "Peritoneal Dialysis Using Bicarbonate–Containing Solution Sterilized by Ultrafiltration," in *The International Journal of Artificial Organs*, vol. 14, No. 8, 1991, pp. 463–465.

*Primary Examiner*—John C. Bleutge
*Assistant Examiner*—Robert H. Harrison
*Attorney, Agent, or Firm*—Thomas S. Borecki; Charles R. Mattenson; Robert M. Barrett

[57] ABSTRACT

The present invention provides improved methods for manufacturing solutions including medical solutions. To this end, in an embodiment, a method for preparing a medical solution is provided comprising the steps of: placing a solution in a gas permeable container; and allowing carbon dioxide to permeate through the container until a desired pH is achieved.

37 Claims, No Drawings

METHOD OF MANUFACTURING AND STORING SOLUTIONS

BACKGROUND OF THE INVENTION

The present invention relates generally to the manufacture, storage, and creation of solutions. More specifically, in an embodiment, the present invention relates to the manufacture, storage, and creation of medical solutions that are administered to patients.

It is known in treating a variety of disease states, and even in order to maintain the health of a mammal, to administer a medical solution. These medical solutions can be administered either enterally, parenterally, or through the peritoneum. Examples of such solutions include medicaments and pharmaceuticals, nutritional formulations, and dialysis solutions. Especially with respect to solutions that are administered intravenously or through the peritoneum, the pH of the solution is an especially important factor. If the pH of the solution is not substantially similar to the physiological pH difficulties can be encountered.

It is known, for example, to use dialysis to support a patient whose renal function has decreased to the point where the kidneys no longer sufficiently function. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood.

In peritoneal dialysis, the patient's own peritoneum is used as a semi-permeable membrane. The peritoneum is the membranous lining in the body cavity that, due to its large number of blood vessels and capillaries, is capable of acting as a natural semi-permeable membrane.

In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows a proper acid-base electrolyte and fluid balance to be returned to the blood. The dialysis solution is simply drained from the body cavity through the catheter.

In order to create an osmotic gradient, the dialysis solution includes an osmotic agent. Although a variety of osmotic agents have been used and considered, typical dialysis solutions include dextrose as an osmotic agent.

It is known in dialysis solutions to also use a buffer. Common buffers used in dialysis solutions are bicarbonate, lactate, and acetate. While initially bicarbonate was the primary buffer considered for use in dialysis solutions, over time, lactate and acetate have been substituted for bicarbonate. This was due to the difficulty in the preparation of bicarbonate-buffered solutions. Lactate and acetate buffers were found to provide greater stability in use over the previous bicarbonate-buffered solutions. See European Patent Application No. 90109963.0.

However, bicarbonate ions provide advantages over lactate or acetate ions. Additionally, experiments indicate that patients exhibit a better tolerance for bicarbonate dialysis solutions. Indeed, certain treatments may require sterile dialysis solutions containing bicarbonate. For example, patients suffering from hypotension and lactate acidosis should receive a bicarbonate-buffered dialysis solution. See, T. S. Ing. et al, "Bicarbonate-Buffered Peritoneal Dialysis", *The International Journal of Artificial Organs*, Vol. 8, No. 3, p. 121 (1985).

Although bicarbonate functions as a buffer, certain issues are raised when using same. In solution bicarbonate is at equilibrium with $CO_2$ gas which easily escapes from the solution. When $CO_2$ gas escapes from the solution, carbonate is generated and the pH of the solution increases.

To avoid this phenomenon, it has been suggested to store bicarbonate in powdered form until just before use. See U.S. Pat. No. 4,489,535. See also European Patent Application No. 0278100 for machine control dialysis.

Alternatively, an impermeable barrier has been proposed to protect the solution. Likewise, methods and containers have been developed for the stabilization of bicarbonate solutions. See U.S. Pat. No. 5,383,324 entitled: "METHOD FOR MANUFACTURING AND STORING STABLE BICARBONATE SOLUTIONS", filed on Apr. 23, 1993.

An additional issue is that in dialysis solutions, dextrose is typically utilized as an osmotic agent. However, like other medical solutions, dialysis solutions must be sterilized before they are administered to a patient. Dextrose, unless it is maintained at an acidic pH, when sterilized, will caramelize. But, on the other hand, bicarbonate must be maintained at a basic pH.

Accordingly, in the art, many attempts have been made to segregate bicarbonate and dextrose so that the two solutions can be maintained at proper pHs when sterilized, e.g., one at a basic pH and the other at an acidic pH. See, for example, U.S. Pat. No. 5,431,496 entitled: "MULTIPLE CHAMBER CONTAINER."

The above issue not only exists with respect to dialysis solutions, but other medical solutions, and indeed, even in the food industry. For example, in many solutions, it would be desirable to initially maintain the solution at a low pH for sterilization and then adjust the solution to a higher, more physiological, pH before the solution is infused into a patient.

However, heretofore, no easy method existed for maintaining a single solution at a reduced pH for sterilization and then without the addition of a composition increasing the pH before infusion.

SUMMARY OF THE INVENTION

The present invention provides improved methods for manufacturing liquid products (solutions).

To this end, a method for preparing a product is provided comprising the steps of: providing a product having a pH that is at least as great as a desired final pH level; lowering the pH of the product below the desired final pH level; and allowing the pH of the product to increase over time toward the desired final pH level due to the release of carbon dioxide from the product.

In an embodiment, the method includes the steps of: providing a solution having a pH of less than 7.0; and adding a component to increase the pH of the solution to at least the desired final level before the step of lowering the pH.

In an embodiment, the step of lowering the pH of the solution includes the step of adding carbon dioxide to the solution.

In an embodiment, the solution is a medical solution.

In an embodiment, the solution is for use in the food industry.

In another embodiment, a method for preparing a liquid is provided comprising the steps of: providing a liquid including carbon dioxide; housing the liquid in a gas permeable container; and allowing carbon dioxide to permeate out through the container until a desired pH of the liquid is achieved.

In another embodiment, a method for preparing a solution is provided comprising the steps of: providing a solution including a carbon dioxide generating composition; placing the solution in a gas permeable container; and allowing carbon dioxide to permeate out through the container until a desired pH of the solution is achieved.

In an embodiment, a method for creating a medical solution is provided comprising the steps of: creating a medical solution that has a pH of less than 7; adding to the solution a carbon dioxide generating composition that increases the pH of the solution; adding a composition that reduces the pH of the solution; and housing a resultant solution in a gas permeable container.

In an embodiment, the carbon dioxide generating composition is sodium bicarbonate.

In an embodiment, the composition for reducing the pH is an acid.

In an embodiment, the resultant solution is stored in the gas permeable container for a time sufficient to allow sufficient carbon dioxide to permeate out of the container to cause the pH of the solution to increase.

In an embodiment, the resultant solution has a pH of less than 6.0.

In an embodiment, the pH of the solution increases to at least 7.0.

In an embodiment, the medical solution is a dialysis solution. In a further embodiment, the dialysis solution includes as an osmotic agent, dextrose.

In an embodiment, the container, including the solution, is exposed to sonication to reduce the time needed to reach a desired pH.

In an embodiment, the container, including the solution, is placed in a reduced atmosphere to decrease the time needed to reach a desired pH.

In an embodiment, an overpouch is placed over the container. In a further embodiment, a carbon dioxide absorber is placed between the container and the overpouch.

In still a further embodiment, a method for preparing a medical solution is provided comprising the steps of: providing a medical solution that has a pH of less than 7; adding to the solution a component that increases the pH of the solution; adding to the solution carbon dioxide to reduce the pH; and housing the solution in a gas permeable container.

In an embodiment, the component that increases the pH of the solution is sodium bicarbonate.

In an embodiment, the medical solution is a dialysis solution.

In an embodiment, the container is placed in an overpouch.

In another embodiment, a method for creating a peritoneal dialysis solution is provided comprising the steps of: preparing a dialysis solution including an osmotic agent, electrolytes, and sodium bicarbonate, the solution having a pH of less than or equal to 6; placing the dialysis solution in a gas permeable container; and allowing sufficient carbon dioxide to permeate out of the container to cause the pH of the solution to increase to at least 7.0.

In still another embodiment, a method for creating a peritoneal dialysis solution is provided comprising the steps of: preparing a dialysis solution including an osmotic agent, electrolytes, and sodium bicarbonate, the solution having a pH of less than or equal to 6; placing the dialysis solution in a gas permeable container; sterilizing the solution including dextrose; and allowing sufficient carbon dioxide to permeate the container to cause the pH of the solution to increase to at least 7.0.

An advantage of the present invention is to provide an improved method for manufacturing liquid products.

Further, an advantage of the present invention is to provide an improved method for manufacturing medical solutions.

Furthermore, an advantage of the present invention is that it provides improved medical solutions.

Another advantage of the present invention is to provide an improved peritoneal dialysis solution.

Still further, an advantage of the present invention is to provide an improved method for manufacturing peritoneal dialysis solutions.

And an advantage of the present invention is that it provides a peritoneal dialysis solution wherein the solution can be sterilized at a reduced pH.

Moreover, an advantage of the present invention is that it provides a peritoneal dialysis solution that does not have to be maintained as two separate parts during sterilization.

Additionally, an advantage of the present invention is to provide a method for manufacturing and storing a dialysis solution that includes bicarbonate and dextrose.

Further, an advantage of the present invention is that it provides improved methods for manufacturing products for the food industry.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides improved methods for creating, manufacturing, and maintaining liquid products. In a preferred embodiment set forth below, the present invention is directed to methods for manufacturing medical solutions and specifically peritoneal dialysis solutions. However, it should be appreciated that the present invention can be used to manufacture and store any medical solution including peritoneal dialysis, hemodialysis, parenteral, and enteral solutions, as well as to manufacture and store liquid food products such as juices.

Pursuant to the present invention, a liquid (solution) is created that includes carbon dioxide. The carbon dioxide can either be present as carbon dioxide gas in the liquid or generated therein by a carbon dioxide generating compound. The pH of the liquid is increased over time due to the release of carbon dioxide from the solution. This increases the pH of the liquid allowing the liquid to initially be stored at a lower pH that increases to a desired pH over time.

As noted above, carbon dioxide is either added to the solution during its preparation or a carbon dioxide generating component is added thereto. In an embodiment, the present invention utilizes a chemical that in solution generates carbon dioxide. Any such chemical that is physiologically acceptable can be used including sodium bicarbonate, sodium carbonate, diethyl malonic acid, diethyl carbonate, carbon dioxide gas itself, or other carbon dioxide generating compositions. Because the solution, pursuant to the present invention, is maintained in a carbon dioxide ($CO_2$) permeable container, the pH of the solution will increase over time due to the loss of carbon dioxide.

In a preferred embodiment of this embodiment of the method of the present invention, sodium bicarbonate is utilized in the solution. Sodium bicarbonate will lose $CO_2$ through a gas permeable container. In this regard, the equilibrium of the bicarbonate is as follows:

$$CO_2 + H_2O \rightleftharpoons H_2CO_3 \rightleftharpoons HCO_3^- + [H+]$$

Accordingly, as carbon dioxide permeates the container, the equilibrium will shift to the left using up hydrogen. This will increase the pH of the solution. Over time, the pH of the solution will stop at a certain level.

For example, utilizing a peritoneal dialysis solution, the solution can include dextrose and be manufactured at a lower pH than usual. In this regard, a peritoneal dialysis solution including dextrose can be manufactured at a pH of 5.0–5.3. Then, sufficient sodium bicarbonate is added to the solution such that the pH is adjusted back to a specific desired level, e.g., 6.0 to 7.6. Then utilizing an acidic compound such as HCl, the solution is adjusted back down to a lower pH, e.g., of 5.0–5.3.

The solution is then filled in a carbon dioxide permeable containers. A number of plastic materials are carbon dioxide permeable and can be used to construct the container. An example of such a container that can be used is the Viaflex® container available from Baxter Healthcare Corporation that is constructed from polyvinyl chloride. Preferably, the container will then be enclosed in an overpouch such as a HDPE overpouch. The solution can then be sterilized. For a peritoneal dialysis solution including dextrose, sterilization of the solution at an acidic pH avoids the problems of caramelization of the dextrose.

During sterilization, and definitely after sterilization, the carbon dioxide will permeate through the container. This will shift the equilibrium pursuant to the formula set forth above to the left using up the hydrogens. This will increase the pH of the solution. Over time, the pH will stop at or near the desired pH point.

For certain solutions including those containing dextrose, the pH may start to decrease at higher pH levels due to dextrose degradation acid formulation. By the addition of a buffer such as citrate or histidine, this pH drop can be prevented.

An advantage of this embodiment of the method of the present invention is that only a sufficient amount of sodium bicarbonate, or other chemical that emits carbon dioxide, is added to the solution to counteract the acid formed during sterilization and to raise the pH a desired level. Thus, the present invention allows the sterilization of a solution, such as dextrose at a low pH minimizing degregation and after sterilization allows the pH to increase over time due to the loss of carbon dioxide. This thereby provides at the time of infusion into a patient, a physiological pH.

Another method that can be used pursuant to the present invention is as follows.

A solution is prepared having a pH that is less than a desired final pH. For example, all the components used in a peritoneal dialysis solution (dextrose, electrolytes, and lactate) can be dissolved in water. The pH of this resultant solution depends on the pH of the lactate and is usually between 5.0–5.3.

Then, pursuant to this embodiment of the method, a sufficient amount of base, sodium hydroxide, is added to this solution until the pH is above the desired final pH level (e.g., desired pH 6.0 then adjust to pH 7.0). Then, the pH of the solution is adjusted down using carbon dioxide gas. For example, the pH can be adjusted down to 5.0–5.5.

The solution is then placed in a gas permeable container such as those discussed above. The container can then be, if desired, sterilized. Over time, the carbon dioxide will diffuse from the container increasing the pH of the solution.

If desired, the pH can be reduced with carbon dioxide to an even lower level by keeping the carbon dioxide dissolved in solution. This can be accomplished by: 1) cooling the solution; or 2) keeping the solution under pressure.

The advantage of this method is that it is easier to perform on a large scale and only carbon dioxide is involved. Also, there is less added sodium utilizing this method. However, as compared to the previous method discussed, the pH rise may fall shorter of the desired pH, in a peritoneal dialysis solution, due to bag material leaching acid and dextrose degradation producing acid. And, additionally, because there is less carbon dioxide in this method.

A still further embodiment of the method is as follows. A solution is prepared. For example, all of the components found in a typical peritoneal dialysis solution (dextrose, electrolytes, and lactate) are dissolved in water. The pH of this resultant solution depends on the pH of the lactate and is usually between 5.0–5.3. Then, a sufficient amount of base, sodium hydroxide, is added to the solution until the pH is above a desired final pH level (e.g., adjust to pH 7.0).

One then adds and dissolves a sufficient amount of a carbon dioxide releasing component (e.g., diethyl malonic acid, diethyl carbonate, etc.). The solution is then filled into a gas permeable container and the container can be sterilized. During sterilization the carbon dioxide releasing component will release carbon dioxide gas decreasing the pH, preferably to 5.0–5.5. After sterilization, the carbon dioxide gas will, leave the system and the pH will increase.

The initial pH adjusted down to described in step 3) for both methods is important. The higher the initial pH (e.g., 5.5–5.7), the faster the post sterilized pH reaches its desired level. However, the downside to a higher initial pH is the increased dextrose degradation and more color formation. At the lower initial pH's (e.g., 5.0–5.4), it is more difficult to keep carbon dioxide in solution. Also, it takes longer to reach the desired post sterilized pH.

A manufacturer can obtain lactate in a wide range of pH's from 3.5–8.5. Therefore, the starting pH, before adjustment, of a solution can range from 3.5–8.5 (we get 5.0–5.3). If one were to purchase lactate at the final desired pH (e.g., 7.0), there would be no need for step 2 in any of the methods.

In order to reduce the time the solution requires to reach the desired pH, a number of modifications to the process can be used. The container housing the solution can be exposed to sonication. This will cause an agitation to the solution increasing the loss of carbon dioxide through the container. The sonication can be achieved by a variety of means including mechanical or sound.

In the alternative, the containers can be placed in a reduced atmosphere, i.e., under vacuum. This will also increase the rate at which carbon dioxide leaves the container reducing the time required for the solution to reach the desired pH.

By locating a carbon dioxide gas absorber between the container and overpouch, one can also increase carbon dioxide diffusion and speed up the process of increasing the pH. A variety of carbon dioxide absorbers can be used including packets of NaOH or KOH.

By selecting materials that are even more gas permeable than PVC, one can further increase carbon dioxide diffusion and reduce the time to reach a desired pH. On the other hand, by selecting materials that are not as gas permeable as PVC, one can increase the time necessary to increase the pH. Likewise, by varying the container/overpouch shape to maximize surface area to volume carbon dioxide, diffusion can be increased.

Additionally, sterilizing the container without the overpouch and maintaining the container outside of the overpouch after sterilization will increase carbon dioxide diffusion.

As noted previously, in an embodiment of the method of the present invention, carbon dioxide gas is added to the solution to adjust the pH of the solution over time. In this regard, if a solution is provided having a pH of 7.0 or less, the pH of the solution is increased to at least a desired final pH level. For example, if the solution had an initial pH of 5.0–5.3, and the solution was provided to a patient, it may be desirable to increase the pH to 6.0 to 7.5.

The pH of the solution is then lowered using carbon dioxide gas. This can be accomplished, for example, by bubbling carbon dioxide into the solution. The pH can be lowered to any level, for example, 5.0–5.5.

The solution is housed in a gas permeable container. As the carbon dioxide permeates the container during storage, the pH of the solution will increase toward the desired final pH.

By way of example, and not limitation, examples of the present invention will now be set forth.

EXAMPLE NO. 1

Three different experiments were performed. A comparison of the parameters that were adjusted during each of these three experiments is presented in Table 1 below. The procedure these experiments used was essentially the same:

1) A Dianeal® dialysis solution with dextrose, available from Baxter was manufactured following typical Baxter procedures.

2) TO the solution was added an amount of sodium bicarbonate to the batch of Dianeal to reach a final desired pH (e.g., 7.0).

3) The pH of the Dianeal solution was adjusted back down to the identified presterilized pH with hydrochloric acid.

4) The bags of Dialysis solution were steam sterilized at 121° C.

5) The sterilized bags were housed at room temperature and/or 40° C.

6) At identified intervals, the bags were pull from the appropriate temperature.

7) The bags were tested for various chemical and physical properties, e.g., pH measurements.

Only pH data associated with each of these three studies appears in Table 2 below. This pH data demonstrates the concept of the present invention. The conclusions for each of these three studies appears below.

Study I (a) This study demonstrated that the pH would increase over time.

(b) The pH would attain a higher value faster if it started out higher initially (compare initial pH's of 5.5 and 6.0).

(c) pH's>6.50 were obtained in less than 1 month.

(d) The lower the initial pH the less color was formed upon sterilization.

Study II (a) This study demonstrated that the pH would increase over time.

(b) The pH would attain a higher value faster if it started out higher initially (compare initial pH's of 5.3 and 5.5).

(c) The lower the initial pH the less color was formed upon sterilization.

(d) A headspace in the solution bag did not affect the time needed to reach the final pH.

(e) In the long term the pH drifted downward indicating a need for a buffer to maintain the pH in the long term.

Study III (a) The study demonstrated that the pH would increase over time.

(b) The lower the initial dextrose concentration the less color was formed upon sterilization.

(c) Although the buffer and its concentration used in this study did not prevent the long term decline in the pH after it had moved upward. Another pH or higher concentration of citrate will maintain the pH.

TABLE 1

Study Parameter Comparison

| Parameter | Study 1 | Study 2 | Study 3 |
| --- | --- | --- | --- |
| Electrolyte profile | Dianeal PD-2 | Dianeal PD-2 | Dianeal PD-2 |
| Dextrose concentration | 4.25% | 4.25% | 2.50% |
| Sodium Bicarbonate concentration | 0.88 g/L | 2.6 g/L | 1.7 g/L |
| Initial pH(s) | 6.0 & 5.5 | 5.5 & 5.3 | 5.2 |
| Bag size | 250 mL | 2000 mL | 1000 mL |

TABLE 2 pH Results Citrate

| Study No. | Initial pH | Buffer (Y/N) | Headspace (cc) | Storage Temp. (C.) |
| --- | --- | --- | --- | --- |
| 1 | 6.0 | N | NC | 25 |
| 1 | 5.5 | N | NC | 25 |
| 2 | 5.3 | N | 0 | 25 |
| 2 | 5.3 | N | 45 | 25 |
| 2 | 5.3 | N | 0 | 40 |
| 2 | 5.3 | N | 45 | 40 |
| 2 | 5.5 | N | 0 | 25 |
| 2 | 5.5 | N | 45 | 25 |
| 2 | 5.5 | N | 0 | 40 |
| 2 | 5.5 | N | 45 | 40 |
| 3 | 5.2 | N | NC | 25 |
| 3 | 5.2 | N | NC | 40 |
| 3 | 5.2 | Y | NC | 25 |
| 3 | 5.2 | Y | NC | 40 | pH Results Approximate Time Interval (Days)

| | 1 | 21 | 30 | 45 | 60 | 75 | 90 | 135 | 180 |
| --- | --- | --- | --- | --- | --- | --- | --- | --- | --- |
| 1 | | | 7.26 | | | | | | |
| 1 | 5.75 | | 6.71 | | | | | | |
| 2 | 5.39 | 5.95 | | | | | 6.13 | | 5.88 |
| 2 | 5.44 | 5.97 | | | | | 6.13 | | 5.90 |
| 2 | | 6.17 | | | | | 5.71 | | |
| 2 | | 6.18 | | | | | 5.71 | | |
| 2 | 5.66 | 6.63 | | | | | 6.98 | | 6.49 |
| 2 | 5.67 | 6.62 | | | | | 6.98 | | 6.66 |
| 2 | | 6.98 | | | | | 6.19 | | |
| 2 | | 6.95 | | | | | 6.08 | | |
| 3 | 5.50 | | | 6.94 | | 7.00 | 6.99 | 7.09 | 6.68 |
| 3 | | | 6.62 | | 6.46 | | 6.55 | 5.98 | |
| 3 | 5.46 | | | 6.91 | | 6.95 | 6.96 | 7.25 | 6.66 |
| 3 | | | 6.76 | | 6.20 | | 6.53 | 5.99 | |

Blank spaces indicate that testing was not scheduled for that interval.
The time intervals are approximate (e.g., 180 is actually 174 days for Study #2 and 190 days for Study No. 3)
NC = No control of headspace was monitored.

EXAMPLE NO. 2

The following methods were used:

Method 1

All components found in Dianeal were dissolved (dextrose, electrolytes, and lactate) in water. The pH of this resultant solution depends on the pH of the lactate and is usually between 5.0–5.3.

Add and dissolve sufficient solid sodium bicarbonate to this solution until the pH reaches the desired final pH level (e.g., 7.0).

pH adjust down to 5.0–5.7 with HCl $CO_2(g)$ or another acid.

Fill into bags and sterilize.

Method 2

All components found in a Dianeal peritoneal dialysis solution (dextrose, electrolytes, and lactate) were dissolved in water. The pH of this resultant solution depends on the pH of the lactate and is usually between 5.0–5.3.

Add a sufficient amount of base, sodium hydroxide, to this solution until the pH is above the desired final pH level (e.g., desired pH 6.0 then adjust to pH 7.0).

pH adjust down to 5.3–5.5 with $CO_2(g)$ .

Fill into bags and sterilize.

The pH of the solutions were measured over time for solutions made with each method.

during pasteurization and/or storage. This solution would have to be stored in a carbon dioxide permeable container. This could be a HDPE container or a glass container with a HDPE cap. The pH of this acidic fruit juice would then rise over time as carbon dioxide permeated from the solution out of the container.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for creating a medical solution comprising the steps of:

creating a medical solution that has a pH that is less than a desired final pH;

adding a base to the medical solution to increase the pH of the medical solution to at least the desired final pH;

adding carbon dioxide gas to the medical solution causing the pH of the medical solution to be lowered; and housing the medical solution in a gas permeable container.

2. The method of claim 1 including the step of sterilizing the container.

3. The method of claim 1 wherein the medical solution is a peritoneal dialysis solution.

pH Measurements Over Time

| Electrolyte Profile | % Hydrous Dextrose | Added Component | Added Component Amount | Method of Manufacturing |
| --- | --- | --- | --- | --- |
| Dianeal PD-2 | 2.50% | Carbon dioxide | NM-Enough to adjust to pH 5.30 | Method 2 |
| Dianeal PD-2 | 2.50% | Carbon dioxide | NM - Enough to adjust to pH 5.40 | Method 2 |
| Dianeal PD-2 | 4.25% | Carbon dioxide | NM - Enough to adjust to pH 5.33 | Method 2 |
| Dianeal PD-2 | 4.25% | Bicarbonate & Carbon dioxide | 0.24 g/L adjust to pH 5.33 | Method 1 |
| Dianeal PD-2 | 4.25% | Bicarbonate & Carbon dioxide | 0.24 g/L adjust to pH 5.33 | Method 1 |

| Electrolyte Profile | Pre-sterilized Initial pH | Bag Size | Interval (days) | | | |
| --- | --- | --- | --- | --- | --- | --- |
| | | | 6 | 13 | 26 | 43 |
| Dianeal PD-2 | 5.30 | 2000 mL | 5.50 | 5.60 | 5.85 | 5.94 |
| Dianeal PD-2 | 5.40 | 2000 mL | 5.57 | 5.67 | 5.86 | 5.96 |
| Dianeal PD-2 | 5.50 | 2000 mL | 5.62 | 5.70 | 5.84 | 5.88 |
| Dianeal PD-2 | 5.33 | 2000 mL | 5.48 | 5.60 | 5.75 | 5.77 |
| Dianeal PD-2 | 5.40 | 2000 mL | 5.81 | 6.19 | 6.76 | 7.47 |
| Dianeal PD-2 | 5.51 | 2000 mL | 5.94 | 6.27 | 6.85 | 7.48 |

NM = Not measured

As previously stated, the present invention can also be used for other liquid products, aside from medical products.

By way of example, many fruit juices are intrinsically acidic (tomato pH 4.4, apple pH 3, lemon pH 2.2). These fruit juices could be pH adjusted to a higher pH with a bicarbonate generating component added. The pH would then be lowered to prevent degradation and color formation 4. The method of claim 1 including the step of allowing sufficient carbon dioxide to permeate out of the container so that the pH of the solution is raised to approximately the desired level.

5. A method for creating a medical solution comprising the steps of:

creating a medical solution that has a pH of less than 7;

adding to the medical solution a carbon dioxide generating composition that increases the pH of the solution;

adding to the medical solution a composition that reduces the pH of the solution; and placing the medical solution in a gas permeable container.

6. The method of claim 5 wherein the carbon dioxide generating composition is selected from the group consisting of sodium bicarbonate, sodium carbonate, diethyl malonic acid and diethyl carbonate.

7. The method of claim 5 wherein the composition for reducing the pH is an acid.

8. The method of claim 5 wherein the medical solution is stored in the gas permeable container for a time sufficient to allow sufficient carbon dioxide to permeate out of the gas permeable container to cause the pH of the medical solution to increase.

9. The method of claim 5 including the step of sterilizing the resultant medical solution.

10. The method of claim 5 wherein the resultant medical solution has a pH of less than 6.0.

11. The method of claim 5 wherein the pH of the medical solution increases to at least 7.0.

12. The method of claim 5 wherein the medical solution is a peritoneal dialysis solution.

13. The method of claim 5 including the step of subjecting the container to sonication.

14. The method of claim 5 including the step of placing the gas permeable container in a reduced atmosphere.

15. The method of claim 5 including the step of placing the gas permeable container in an overpouch.

16. The method of claim 15 including the step of placing a carbon dioxide absorber between the container and the overpouch.

17. The method of claim 16 wherein the carbon dioxide absorber is chosen from the group consisting of NaOH and KOH.

18. The method of claim 15 wherein the gas permeable container is sterilized before it is placed in the overpouch.

19. A method for preparing a medical solution comprising the steps of:

providing a medical solution including a carbon dioxide generating composition;

placing the medical solution in a gas permeable container; and allowing carbon dioxide to permeate out through the container until a desired pH for the medical solution is achieved.

20. The method of claim 19 wherein the medical solution is a peritoneal dialysis solution.

21. The method of claim 19 wherein the carbon dioxide generating composition is sodium bicarbonate.

22. The method of claim 19 including the step of sterilizing the medical solution after it has been placed in the gas permeable container.

23. The method of claim 19 wherein the pH of the medical solution increases to at least 6.0.

24. The method of claim 19 including the step of subjecting the gas permeable container to sonication.

25. The method of claim 19 including the step of placing the gas permeable container in a reduced atmosphere.

26. The method of claim 19 including the step of placing the gas permeable container in an overpouch.

27. The method of claim 19 including the step of placing a carbon dioxide absorber between the container and the overpouch.

28. The method of claim 19 wherein the carbon dioxide generation is carbon dioxide gas.

29. The method of claim 27 wherein the carbon dioxide absorber is chosen from the group consisting of NaOH and KOH.

30. The method of claim 19 wherein the gas permeable container is sterilized before it is placed in the overpouch.

31. A method for creating a dialysis solution comprising the steps of:

preparing a dialysis solution including an osmotic agent, electrolytes, and sodium bicarbonate, the solution having a pH of not greater than 6;

placing the dialysis solution in a gas permeable container; and allowing sufficient carbon dioxide to permeate out through the gas permeable container to cause the pH of the dialysis solution to increase to at least 6.0.

32. The method of claim 31 including the step of sterilizing the dialysis solution after it is placed in the gas permeable container.

33. The method of claim 31 wherein the osmotic agent is dextrose.

34. The method of claim 31 including the steps of adding a carbon dioxide generating compound to the dialysis solution.

35. The method of claim 31 wherein a carbon dioxide generating product is added to the dialysis solution to increase the pH of the dialysis solution to a level that is at least as great as a desired final pH level of the dialysis solution.

36. The method of claim 31 wherein a carbon dioxide generating compound is added to the dialysis solution after the dialysis solution has a pH that is at least as great as the desired final pH level.

37. A method for creating a dialysis solution comprising the steps of:

preparing a dialysis solution including dextrose, electrolytes, and sodium bicarbonate, the solution having a pH of less than or equal to 6;

placing the dialysis solution in a gas permeable container;

sterilizing the dialysis solution; and allowing sufficient carbon dioxide to permeate out of the gas permeable container to cause the pH of the dialysis solution to increase to at least 7.0.

* * * * *

UNITED STATES PATENT AND TRADEMARK OFFICE
CERTIFICATE OF CORRECTION

PATENT NO. : 5,605,934
DATED : February 25, 1997
INVENTOR(S) : Giertych

It is certified that error appears in the above-identified patent and that said Letters Patent is hereby corrected as shown below:

Title page item [56], insert

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION | |
|---|---|---|---|---|---|---|---|---|---|---|---|---|---|
| | | | | | | | | | | | | YES | NO |
| | WO | 9 | 1/ | 0 | 80 | 0 | 8 | 06/23/91 | PCT | | | | |
| | | 0 | 6 | 33 | 0 | 1 | 3 A1 | 08/04/94 | EUROPE | | | | |
| | | | | | | | | | | | | | |

OTHER DOCUMENTS

| | | |
|---|---|---|
| | | Feriani et al. "Bicarbonate Buffer for CAPD Solution," in *Transactions of American Society for Artificial Internal Organs,"* Vol. XXXI, 1985, pp. 668-672. |
| | | |
| | | |

Signed and Sealed this

Second Day of March, 1999

Attest:

Attesting Officer

Q. TODD DICKINSON

Acting Commissioner of Patents and Trademarks